United States Patent [19]

Sundqvist

[11] Patent Number: 4,780,898
[45] Date of Patent: Oct. 25, 1988

[54] ARRANGEMENT IN A GAMMA UNIT

[75] Inventor: Hans Sundqvist, Vikingstad, Sweden

[73] Assignee: Elekta Instrument, Geneva, Switzerland

[21] Appl. No.: 44,217

[22] Filed: Apr. 30, 1987

[30] Foreign Application Priority Data

Apr. 30, 1986 [SE] Sweden .............................. 86020252

[51] Int. Cl.$^4$ ............................................. A61N 5/10
[52] U.S. Cl. ................... 378/65; 250/496.1; 378/195; 378/68; 378/9
[58] Field of Search ............... 378/9, 10, 119, 120, 378/149, 195, 65; 250/496.1; 378/195, 65

[56] References Cited

PUBLICATIONS

Borje Larsson, Kurt Liden and Bert Sarby, "Irradiation of Small Structures through the Intact Skull", ACTA Radiological, Official Organ of the Radiological Societies of Denmark, Finland, Norway and Sweden, vol. 13, Dec. 1974, pp. 527–534.

Lars Leksell, "Stereotatic Radiosurgery", London British Medical Assoc ., Travistock Square, WC1H9JR, Reprinted from Journal of Neurology Neurosurgery and Psychiatry, vol. 46, No. 9 pp. 797–803. Sep. 1983.

Hans Dahli, Bert Sarby, "Destruction of Small Intracranial Tumurs with Co GAMMA Radiation", Physical and Technical Considerations, vol. 14, Fasc. 3, 1975 Jun., pp. 210–227.

*Primary Examiner*—Carolyn E. Fields
*Assistant Examiner*—John A. Miller
*Attorney, Agent, or Firm*—Browdy and Neimark

[57] ABSTRACT

An arrangement in a gamma unit, comprising a large number of radiation sources (9) mounted within a radiation shield (2) and having beam channels (6, 19) directed radially from said radiation sources toward a common focal point (F), said radiation shield comprising a space adapted to accommodate the head of a patient resting on a support.

The novel matter resides in that the radiation sources (9) and the beam channels (6, 19) directed radially therefrom toward the focal point are located, in relation to the diametrical plane through the opening to the space, within a zone extending to latitudes 30°–45°, as seen from said diametrical plane.

6 Claims, 3 Drawing Sheets

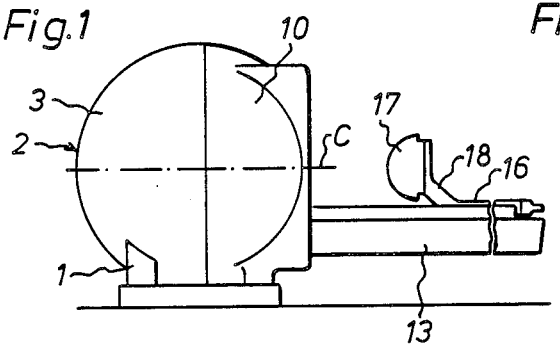
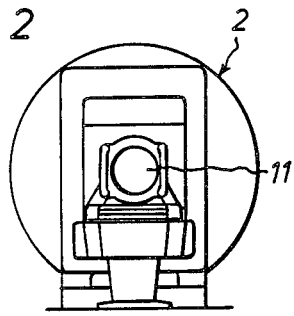
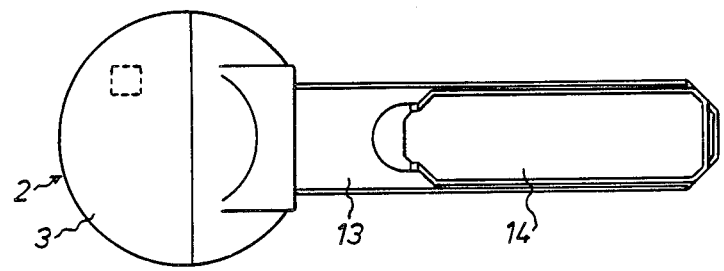

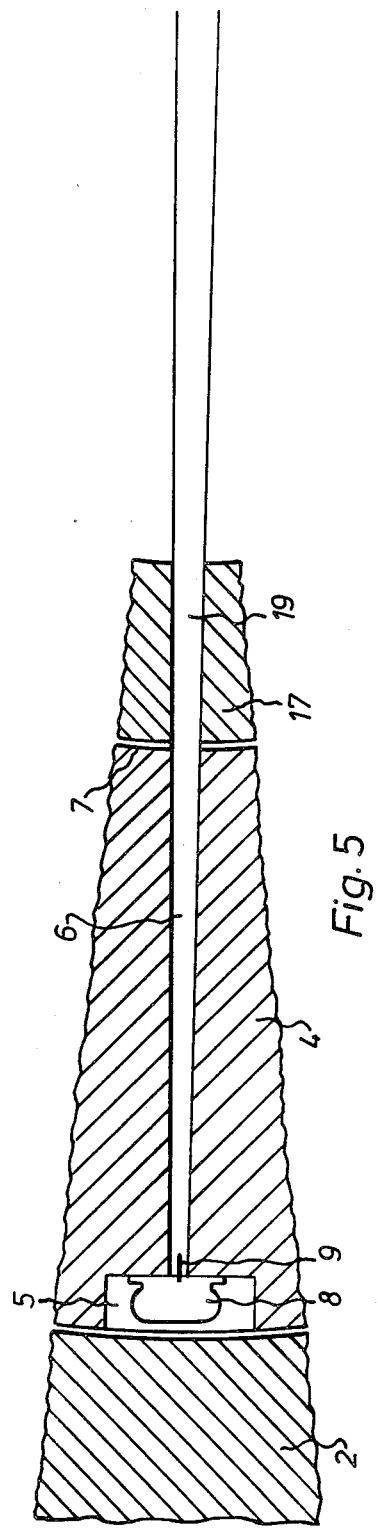

ARRANGEMENT IN A GAMMA UNIT

BACKGROUND OF THE INVENTION

1. Field of the Invention

The present invention relates to an arrangement in a gamma unit, comprising a large number of radiation sources mounted within a radiation shield and having beam channels directed radially from said radiation sources toward a common focal point, said radiation shield comprising a space adapted to accommodate the head of a patient resting on a support.

2. The Prior Art

Gamma units of the above-mentioned type are previously known from, for example, ACTA RADIOLOGICA; Vol. 13:1974, "Irradiation of small structures through the intact skull", ACTA RADIOLOGICA, Vol. 14:1975, "Destruction of small intracranial tumours with $^{60}$Co gamma radiation" and JOURNAL OF NEUROLOGY, NEUROSURGERY & PSYCHIATRY, Vol. 46:1983 "Stereotactic Radiosurgery".

In the prior art arrangements, the center axis of the central member makes an angle of 55° with the patient's longitudinal axis and the horizontal plane, and the beam channels have a varying distribution in respect of both position and number about this center axis. In known and planned gamma units, the beam channel distribution has varied between ±30° to ±51° in one plane and about ±80° in the other. In these prior art arrangements, some beams will approach the longitudinal axis of the patient so that there is a certain risk that scattered radiation and an occasional primary beam will reach the surroundings when the door toward the central member is opened.

SUMMARY OF THE INVENTION

The present invention aims at providing a novel type of gamma unit adapted to the mode of operation of CT (Computer Tomography) and NMR (Nuclear Magnetic Resonance) machines which give cross-sections of the examined part of the body and minimise the risk of scattered radiation.

The novel matter of the arrangement according to the invention resides in that the radiation sources and the beam channels directed radially therefrom toward the focal point are located, in relation to the diametrical plane across the opening to said space, within a zone extending to latitudes 30°-45°, from said diametrical plane.

BRIEF DESCRIPTION OF THE DRAWINGS

An embodiment of a gamma unit arranged in accordance with the invention will be described below, reference being had to the accompanying drawings in which:

FIGS. 1, 2 and 3 are schematic lateral views of the outer construction of the arrangement;

FIG. 5 is a section on an even larger scale of a cut-out portion comprising a beam channel.

DETAILED DESCRIPTION OF THE PREFERRED EMBODIMENT

Figure 4:
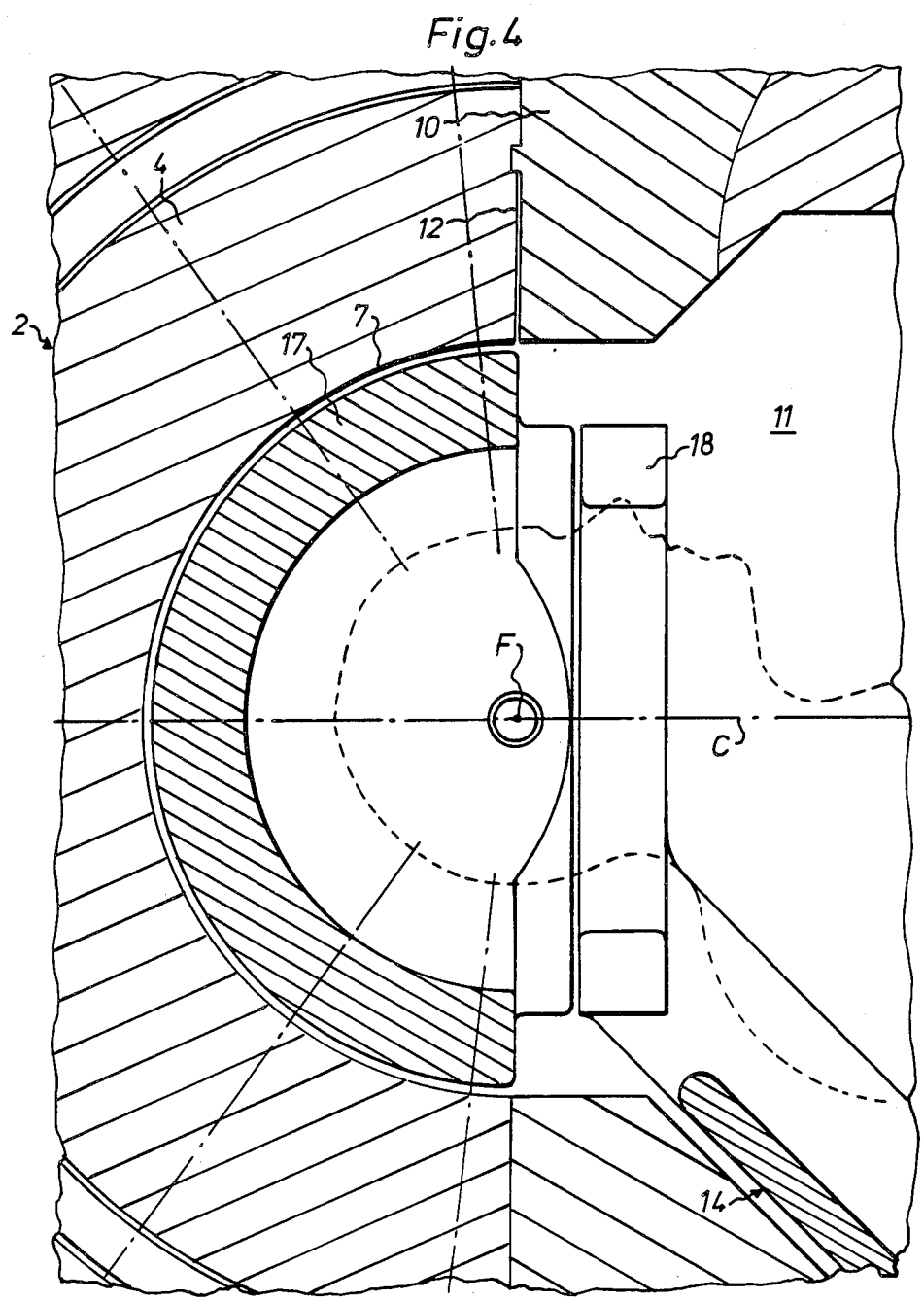
FIG. 4 is a vertical section on a larger scale of the portion around the central member and the helmet.

A frame 1 supports the essentially spherical radiation shield 2 which is divided into two halves along a vertical plane. One half 3 accommodates, in a semispherical space, the central member 4 which has a semispherical outer surface and a semispherical inner surface.

In the outer surface, and in an essentially annular portion adjacent the edge of the semipherical central member 4, a large number of seats 5 are arranged, from which radially extending beam channels 6 are extending inwardly toward the inner surface 7 of said central member. The beam channels 6 are slightly widened toward the inner surface of the central member, and all channels are so directed that their axes converge at the center of said member, the focal point F being located in the same plane as the edge of said central member.

At the outer end of each beam channel 6, a bushing 8 is provided in the seat 5, said bushing carrying the radiation source 9 which preferably is a cobalt 60 isotope.

The beam channels are located within an annular portion adjacent the free edge of the central member and have an inward extent amounting to 30°-45°, as is shown in FIG. 4. In other words, the beam channels are located within an annular curved zone extending maximally up to latitudes 30°-45°, as seen from the diametrical plane.

In the other half 10 of the radiation shield, a through opening 11 is provided which extends up to the plane of intersection 12 between the two halves and thus opens into the interior of said central member. From the lower edge at the outer end of the opening, a frame 13 provided with guides for a bed-like support 14 carrying the patient is extending.

The two halves of the radiation shield 2 are carefully and precisely fitted together and have, on their opposing surfaces, complementary lands and grooves to make the connection radiation safe.

The patient support 14 is mounted on wheels travelling in the guides of the frame 13 and comprises an elongate bed-like surface 16 on which the patient is lying. The helmet 17 is supported by a bracket 18 secured to the support 14. The helmet 17 has an outer shape carefully adapted to the shape of the inner surface of the central member 4 and can be inserted therein with a clearance of some millimeters. Mounted in the helmet are a number of radial channels 19 corresponding to the number of beam channels 6 in the central member 4, said channels 19 being exactly aligned with the channels 6 in said central member when the helmet 17 has been inserted therein. The channels 19 form nonadjustable apertures defining the dimension of the beams passing therethrough to the patient to be treated. Thus, an uninterrupted path of radiation extends from the respective radiation source radially toward the focal point F within the helmet 17 in the diametrical plane thereof. Mounted within the helmet are attachments for a so-called stereotactic instrument, i.e. a device defining the position of the area to be treated. During treatment, the patient's head is fixed in a position such that the radiation focal point coincides with the said treatment area.

According to the invention, the geometrical central axis c of both the central member 4 and the helmet 17 is horizontal and thus essentially parallel with the longitudinal axis of the patient. The central axis may also be said to form a normal toward the vertical plane through the opening in the radiation shield.

As has been mentioned above, the beam channels 6 and 19, respectively, are arranged in an annular portion of the semispherical central member adjacent the edge thereof so that geometrical axis of the beam channels converge in a point, the focal point, located in the vertical plane through the edge of the central member and the helmet and lie within a portion extending up to 30°–45° from the vertical plane. As a result, no beams will be directed outwardly through the opening 11 of the radiation shield, and all beams that have passed the focal point will impinge solely upon the radiation-shielding edges of the said opening.

The arrangement according to the invention reduces the scattered radiation and, because of the reorientation of the central axis and the annular grouping of the beam channels around the outer portion of the central member, is suitable for use with prior art machines for computer tomography (CT) and NMR which illustrate cross-sections of the examined part of the body.

I claim:

1. An arrangement in a gamma unit, comprising a plurality of radiation sources mounted within a radiation shield and having beam channels directed radially from said radiation sources toward a common focal point, said radiation shield comprising a space for accommodating the head of a patient lying on a support, and having an opening, the radiation sources and the beam channels directed radially from said space toward the focal point being located, in relation to the diametrical plane extending across the opening to said space, only within a zone extending between latitudes 30°–45°, as seen from said diametrical plane.

2. An arrangement as claimed in claim 1, the radiation sources are arranged in seats adjacent the outer surface of an essentially semispherical central member provided in the space of the radiation shield, said beam channels extending radially from said seats through the central member toward the inner cavity thereof, in which a helmet is insertable which has a number of radial through channels corresponding to the beam channels within said central member and is provided with means for essentially nondisplaceably holding the patient's head, and that the radial channels within said central member and said helmet, which channels extend outwardly from the seats in the outer surface of said central member, are located within curved annular zones of said central member and said helmet, said zones extending only between latitudes 30°–45°, as seen from the essentially vertical diametrical plane through the opening of siad central member and said helmet, respectively.

3. An arrangement as claimed in claim 2, wherein the semispherical central member provided with said radial beam channels from said radiation sources is so located in relation to the position of a patient lying essentially horizontally on the support that its geometrical central axis which is perpendicular to the central plane, is essentially horizontal and parallel and/or coincident with the patient's longitudinal axis.

4. An arrangement as claimed in claim 2, wherein the radiation shield comprises two halves of material with a vertical plane of division, that a semispherical space accommodating the semispherical central member is provided within one radiation shield, while the other radiation shield has a through opening into the interior of said central member, that a bed-like support comprises a bed supporting the patient and movable into said opening, and that the bed at its inner end is provided with a bracket carrying the helmet for supporting the patient's head, said helmet being provided with channels and accommodated by the space within said central member.

5. An arrangement as claimed in claim 4, the channels of the helmet are formed as nonadjustable apertures determining the dimension of the beam penetrating therethrough.

6. An arrangement as claimed in claim 3, wherein the radiation shield comprises two halves of material a vertical plane of division, that a semispherical space accommodating the semispherical central member is provided within one radiation shield, while the other radiation shield has a through opening into the interior of said central member, that a bed-like support comprises a bed supporting the patient and movable into said opening, and that the bed at its inner end is provided with a bracket carrying the helmet for supporting the patient's head, said helmet being provided with channels and accommodated by the space within said central member.

* * * * *

UNITED STATES PATENT AND TRADEMARK OFFICE
CERTIFICATE OF CORRECTION

PATENT NO. : 4,780,898
DATED : October 25, 1988
INVENTOR(S) : Hans Sundqvist

Page 1 of 3

It is certified that error appears in the above-identified patent and that said Letters Patent is hereby corrected as shown below:

The title page, showing an illustrative figure, should be deleted and substitute therefor the attached title page.

Delete Drawing Sheet 2, and substitute therefor the Drawing Sheet, consisting of FIG. 4, as shown on the attached page.

Signed and Sealed this

Twenty-second Day of June, 1999

Attest:

Q. TODD DICKINSON

*Attesting Officer*     *Acting Commissioner of Patents and Trademarks*

United States Patent [19]

Sundqvist

[11] Patent Number: 4,780,898
[45] Date of Patent: Oct. 25, 1988

[54] ARRANGEMENT IN A GAMMA UNIT

[75] Inventor: Hans Sundqvist, Vikingstad, Sweden

[73] Assignee: Elekta Instrument, Geneva, Switzerland

[21] Appl. No.: 44,217

[22] Filed: Apr. 30, 1987

[30] Foreign Application Priority Data

Apr. 30, 1986 [SE] Sweden ............................ 86020252

[51] Int. Cl.⁴ .................................................. A61N 5/10
[52] U.S. Cl. ..................................... 378/65; 250/496.1; 378/195; 378/68; 378/9
[58] Field of Search ...................... 378/9, 10, 119, 120, 378/149, 195, 65; 250/496.1; 378/195, 65

[56] References Cited

PUBLICATIONS

Borje Larsson, Kurt Liden and Bert Sarby, "Irradiation of Small Structures through the Intact Skull", ACTA Radiological, Official Organ of the Radiological Societies of Denmark, Finland, Norway and Sweden, vol. 13, Dec. 1974, pp. 527–534.
Lars Leksell, "Stereotatic Radiosurgery", London British Medical Assoc ., Travistock Square, WC1H9JR, Reprinted from Journal of Neurology Neurosurgery and Psychiatry, vol. 46, No. 9 pp. 797–803. Sep. 1983.
Hans Dahli, Bert Sarby, "Destruction of Small Intracranial Tumurs with Co GAMMA Radiation", Physical and Technical Considerations, vol. 14, Fasc. 3, 1975 Jun., pp. 210–227.

Primary Examiner—Carolyn E. Fields
Assistant Examiner—John A. Miller
Attorney, Agent, or Firm—Browdy and Neimark

[57] ABSTRACT

An arrangement in a gamma unit, comprising a large number of radiation sources (9) mounted within a radiation shield (2) and having beam channels (6, 19) directed radially from said radiation sources toward a common focal point (F), said radiation shield comprising a space adapted to accommodate the head of a patient resting on a support.

The novel matter resides in that the radiation sources (9) and the beam channels (6, 19) directed radially therefrom toward the focal point are located, in relation to the diametrical plane through the opening to the space, within a zone extending to latitudes 30°–45°, as seen from said diametrical plane.

6 Claims, 3 Drawing Sheets

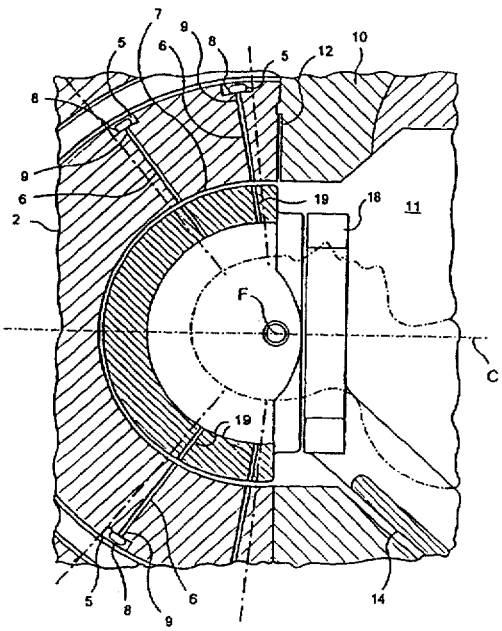

UNITED STATES PATENT AND TRADEMARK OFFICE
CERTIFICATE OF CORRECTION

PATENT NO. : 4,780,898
DATED : Oct. 25, 1988
INVENTOR(S) : Hans Sundqvist

Page 3 of 3

It is certified that error appears in the above-identified patent and that said Letters Patent is hereby corrected as shown below:

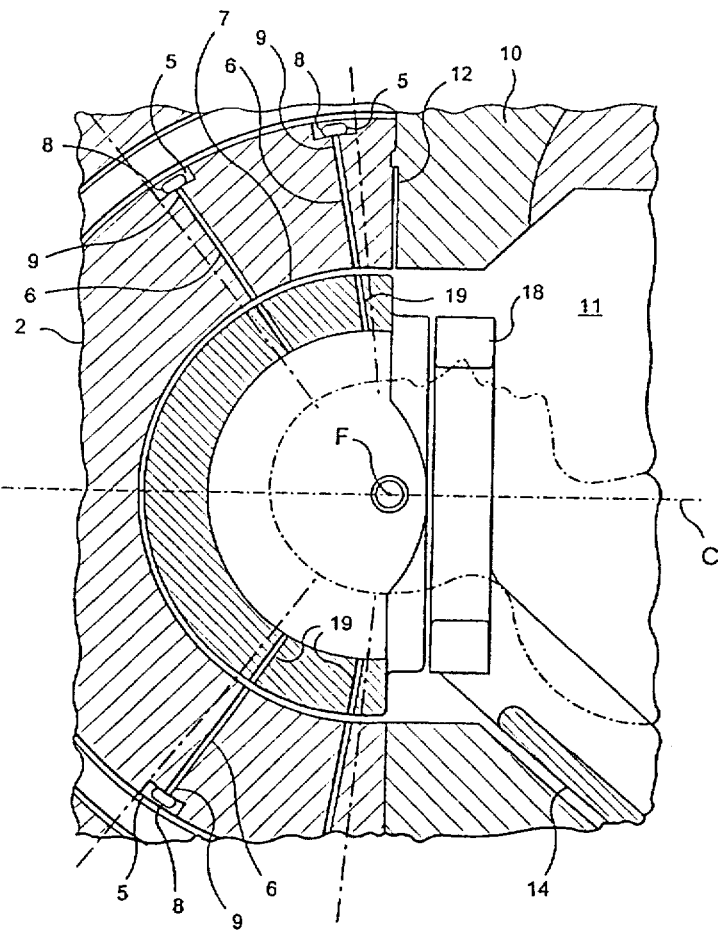

FIG. 4